United States Patent [19]

Glassman

[11] 4,335,720
[45] Jun. 22, 1982

[54] CATAMENIAL TAMPON WITH HOLLOW CORE

[76] Inventor: Jacob A. Glassman, 1680 Michigan Ave., Miami Beach, Fla. 33139

[21] Appl. No.: 138,501

[22] Filed: Apr. 9, 1980

[51] Int. Cl.³ ............................................ A61F 13/20
[52] U.S. Cl. ................... 128/270; 128/263; 128/285
[58] Field of Search ........................ 128/263, 270, 285

[56] References Cited

U.S. PATENT DOCUMENTS

| Re. 27,677 | 6/1973 | Glassman | 128/270 |
| 3,515,138 | 6/1970 | Hochstrasser et al. | 128/270 |
| 3,683,912 | 8/1972 | Olson et al. | 128/285 |
| 3,683,915 | 8/1972 | Voss | 128/285 |
| 4,200,101 | 4/1980 | Glassman | 128/285 |

Primary Examiner—William J. Van Balen
Attorney, Agent, or Firm—Elmer L. Zwickel

[57] ABSTRACT

A catamenial tampon having a hollow core opening onto its insert end and having radial slots at said end in communication with the hollow core. The invention also relates to the method of tampon fabrication and to a tool used in such fabrication.

9 Claims, 13 Drawing Figures

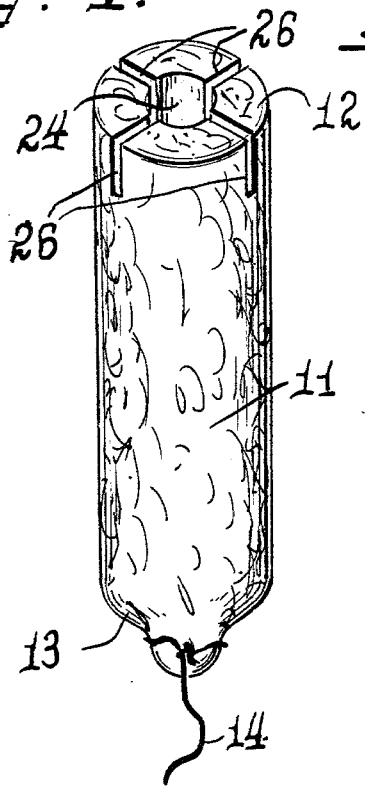
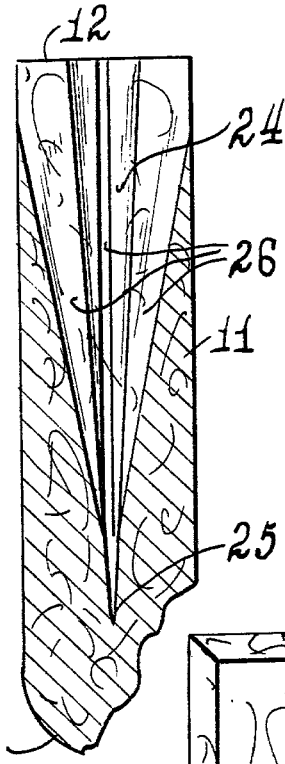
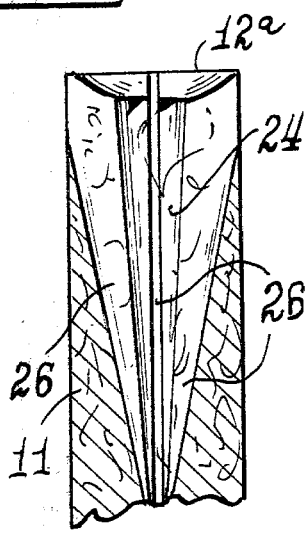
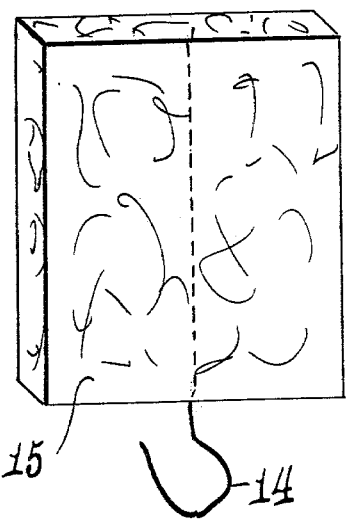
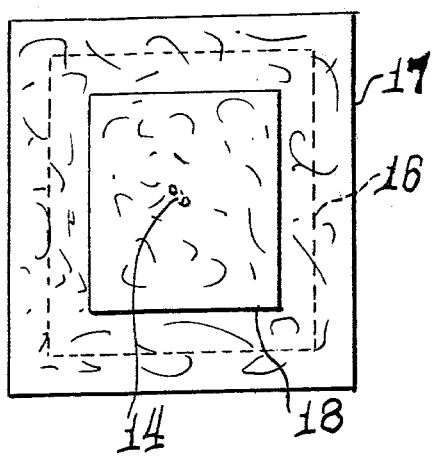
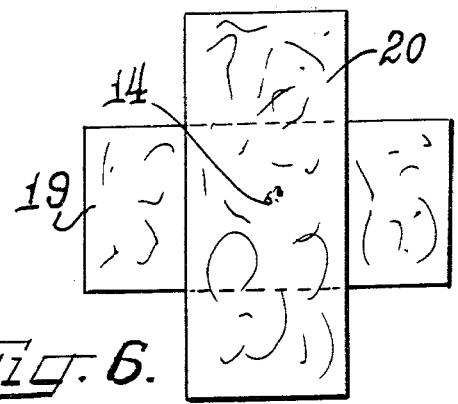

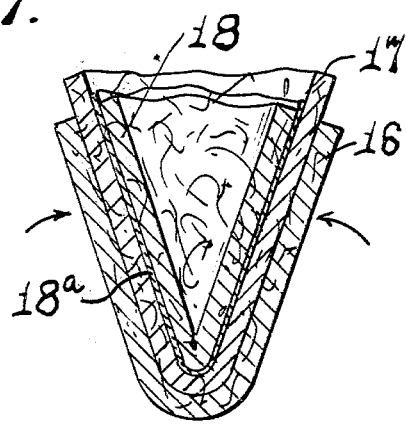
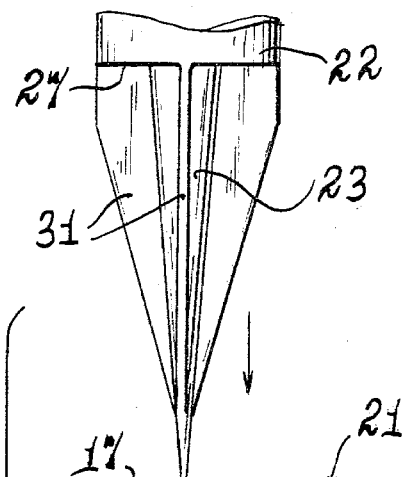
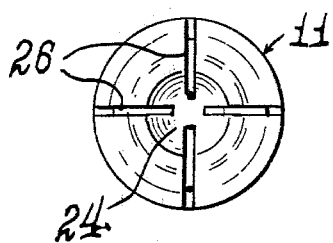
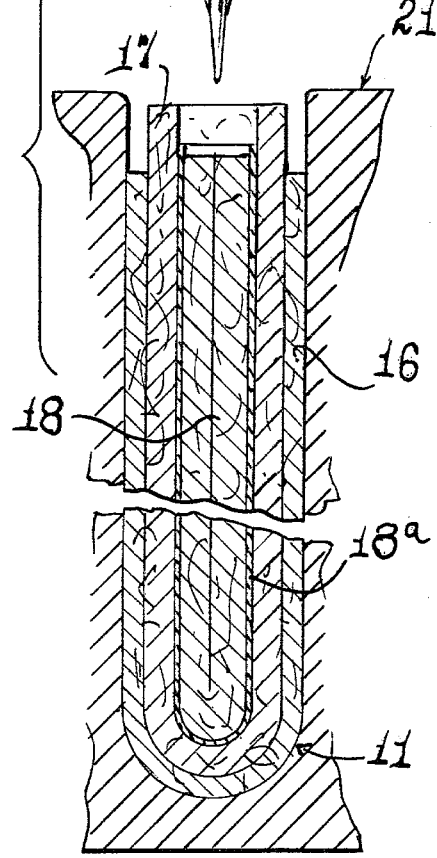
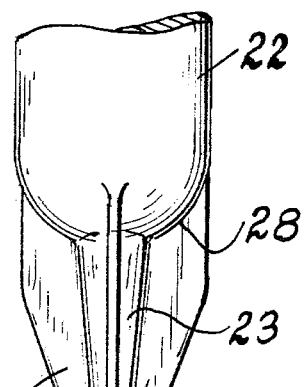
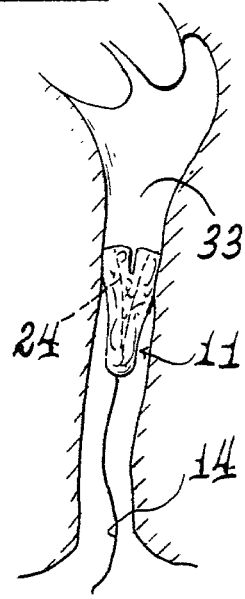
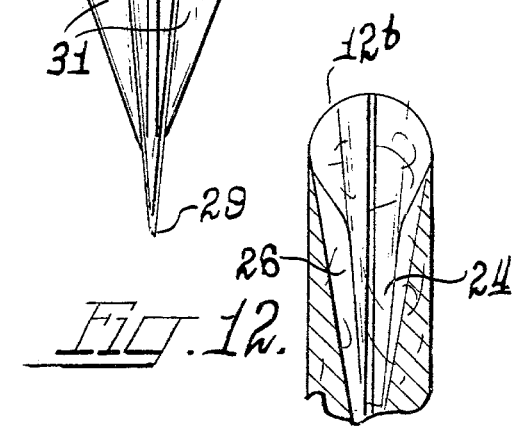
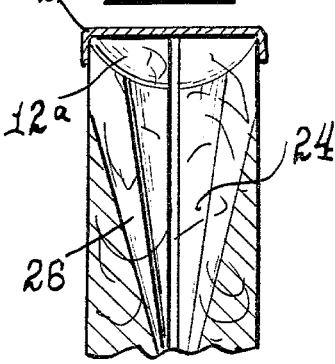

CATAMENIAL TAMPON WITH HOLLOW CORE

This invention relates to improvements in catamenial tampons and to the method of and tool for making same.

More particularly, the improved tampon has a hollow core or axial cavity communicating with its insert end. The core is formed during or after compression of the absorbent material forming the tampon so as to prevent destruction of the hollow core during such compression. Furthermore, the cavity preferably has a series of circumferentially spaced radial slots or channels in communication therewith and which also open onto the insert end of the tampon. These are provided to increase the collection of the maximum quantity of menstrual fluids within the tampon at the insert end and consequently speed expansion or "flowering" of the tampon prior to moisture absorption in the medial and outer end of the tampon. A single novel tool performs this.

The advantage of such structure is readily apparent when it is appreciated that tampons presently available on the market fail to include any worthwhile foolproof structures to hasten moisture absorption or the collection of moisture at the insert end of the tampon. This is true even of those tampons that include structure to theoretically enable the insert end of the tampon to expand or "flower" upon being wetted. In fact, such structures, being initially compacted into an elongated round body are devoid of any central hollow core and fail to "open" or "flower" upon being wetted. Instead, the solid insert end tends to swell and much of the waste fluids initially collect on the insert end and, as their amount increases, they spill over and run down over the outside surface of the tampon. This is the often feared "strike-through".

The objectionable result obtained with conventional tampons is not overcome by the fact that many of such tampons are especially fabricated with the expectation of "flowering" when wetted. Such a tampon is disclosed in Glassman Pat. No. Re-27677, granted June 19, 1973. Other commercial tampons such as, PLAYTEX for example, are fabricated from one or more layers of cotton-like or other unwoven material which are folded upwardly into a cup-shape; or from a single thick pad (KOTEX), either one of which is then compacted into its final elongated round body shape. The compression tends to totally close any axial opening that might have been generated during the forming process, hence no fluid ever reaches the lower interior one-third of the tampon. As a consequence, the tampon utterly fails to prevent premature strike-through, and its useful life is greatly shortened.

It is therefore, an object of the invention to provide a novel catamenial tampon and fabrication tool of the character referred to; and one that is capable of insuring maximum waste-fluid collection within the interior of the tampon at its insert end, and consequently increase the useful life of the tampon and retard "strike-through".

Many additional objects and advantages of the invention will become apparent with reference to the following description and accompanying drawings. IN THE DRAWINGS:

FIG. 1 is an enlarged perspective view of the tampon of the invention;

FIG. 2 is an enlarged axial sectional view of the insert end of the tampon;

FIG. 3 is a view similar to FIG. 2, illustrating the tampon with a concave insert end;

FIG. 4 is a perspective view of one layer or pad of material from which the tampon can be made;

FIG. 5 is a plan view of a multilayered tampon pad;

FIG. 6 is a plan view of another multilayered tampon pad;

FIG. 7 is a central sectional view of the FIG. 5 tampon pad, formed into a cup-shape prior to compression;

FIG. 8 is an enlarged axial sectional view of the FIG. 7 pad compressed and positioned to receive the plunger for forming the hollow core and channels opening onto the insert end of the compressed pad;

FIG. 9 is a top plan view of the insert end of the completed tampon;

FIG. 10 is a fragmentary view of a modified form of plunger and it's carrying rod;

FIG. 11 is an axial sectional view of the insert end of the formed tampon having a removable cover over the cavity formed by the plunger of FIG. 10;

FIG. 12 is a sectional view of the tampon showing it with a convex insert end; and FIG. 13 is a schematic view of the vaginal canal, illustrating the "flowering" of the wetted tampon.

Referring now to the accompanying drawings and particularly to FIGS. 1, 2 and 3, the tampon 11 is comprised of a mass of cotton or other non-woven highly moisture absorbing material to be detailed later herein. The absorbent mass is formed as an elongated round body which may have it's insert end 12 formed flat, as in FIGS. 1 and 2; or it may be formed concave as at 12a (FIG. 3) or convex as at 12b in FIG. 12. The outer end 13 of the tampon body preferably is round as shown and a pull-out string 14 may extend from said end.

The tampon body may be fabricated in a number of ways, several of which are illustrated for example, but not by way of restriction, in FIGS. 4, 5 and 6. In FIG. 4, a one-piece pad 15 (KOTEX) of moisture absorbing material, substantially square or rectangular in shape and of minor thickness, is compacted by compression into a tampon shape substantially as shown in FIG. 1. The FIG. 5 illustration comprises a plurality of layers of moisture absorbing material 16, 17 and 18, laid one upon the other (PLAYTEX) with each layer differing slightly in size. These layers are secured together by anchoring the pull string 14 at their center. FIG. 6 illustrates a pair of rectangular pads of moisture absorbent material 19–20, set at right angles to each other and also then secured together by the pull string 14.

In forming the improved tampon, the pad combination shown in FIGS. 5 and 6 are initially centrally gathered together, as illustrated in the FIG. 7 showing of the FIG. 5 pads, into the substantially cup-shaped formation (FIG. 7). Preferably, a layer 18a of impervious material is inserted between layers 17 and 18 to restrain outward flow of menstrual fluids. This formation is placed in an open die 21 which is then closed (FIG. 8) to compact the absorbent material. It should be obvious that any effort to establish a hollow core in the tampon being formed would be defeated by the die compression which, incidentally, is accompanied by end-wise pressure to insure correct shaping of the tampon. Such end-wise pressure has heretofore been effected by use of a smooth faced plunger rod that acts on the insert end only.

In this disclosure, the plunger rod 22 is modified to include means on it's tampon contacting end to generate a hollow axial core in the tampon. This means comprises a cone-shaped extension 23 on the rod end and which is of such length that it terminates short of the outer end of the tampon. Referring now specifically to FIGS. 2, 3 and 8 and 10, it will be observed that the tampon is formed with an axial hollow core or cavity 24 (FIG. 2) that is substantially cone-shaped with it's apex 25 terminating close to the outer end 13 of the tampon. The hollow core is formed, during or just after die compression of the tampon, and it includes at least one radial slot channel 26 that is in flow communication with the hollow core. Both the hollow core 24 and slot 26 open onto the insert end 12 of the tampon. Should a plurality of slots 26 be provided, as preferred, they will be circumferentially spaced around the hollow core, as best shown in FIG. 9, and may, as shown in FIG. 1, open onto the outside of the tampon wall at the insert end only.

The hollow core and slots are formed by the tool constituting the cone-shaped extension 23, best shown in FIG. 8. This extension is integral with the plunger rod 22 that is connected to a source of reciprocating power (not shown). The rod may have a flat bottom end 27 (FIG. 8) a convex bottom end 28 (FIG. 10) or a concave bottom. The cone-shaped extension 23 terminates in a peak 29 at it's lead end. One or more radially extending wings 31 is provided on the cone-shaped extension. When the plunger rod is depressed to thrust the extension into the tampon body 11, said tampon body is formed with the hollow core 24 and radial slot or slots 26. The presence of a concave bottom on the plunger rod 22 results in the formation of a convex insert end 12b (FIG. 12).

When the tampon is formed with a concave end 12a (FIG. 3) said cavity may be utilized as a container for a medicament, be it a pill, jelly, powder, etc.; and if placed in the cavity by a pharmaceutical house, it may be protected by an adhesively secured cover 32 (FIG. 11) which may be readily removed prior to tampon insertion.

In the light of the foregoing it should be quite evident that when the tampon of the disclosed structures is inserted into the vaginal canal 33 (FIG. 13) the reaction of the tampon, upon being wetted, is to initially expand at its insert end; thus preventing the free passage of menstrual fluids about the outside surface of the tampon and to then continue its expansion along its length by reason of continued flow of fluids into and down within the hollow core. As a consequence, the tampon is totally saturated from the insert end outwardly and there is no accumulation of fluids on the insert end as occurs with other known tampons and hence there is no strike-through by reason of external flow.

Although I have described preferred embodiments of my invention, in considerable detail it will be understood that the description thereof is intended to be illustrative rather than restrictive, as details of the structure, the tool and the method of manufacture, may be modified or changed without departing from the spirit or scope of the invention.

Accordingly, I do not desire to be restricted to the exact construction and method described.

What I claim is:

1. A catamenial tampon comprising a compressed, shape-retaining, generally cylindrical fibrous body having an insert end and an outer end, an axial cavity in said body opening at one end onto the insert end of the body, the cavity having it's surrounding wall tapered inwardly toward and terminating short of the outer end of the body, and at least one radial slot in said wall in flow communication with the cavity, said slot being substantially coextensive with said cavity length and opening at one end onto the insert end of said body.

2. The catamenial tampon recited in claim 1, wherein the slot is of reduced depth as it approaches the outer end of the body.

3. The catamenial tampon recited in claim 1, wherein there are a plurality of such slots in said wall circumferencially spaced around the cavity.

4. The catamenial tampon recited in claim 1, wherein the body is comprised of a plurality of pads of fibrous shape-retaining material drawn into a substantially cup-shaped configuration and compacted into the generally cylindrical shape.

5. The catamenial tampon recited in claim 1, wherein the slot opens onto the outside surface of the body in the area closely adjacent to the insert end.

6. A catamenial tampon, comprising a compressed shape-retaining generally cylindrical fibrous body having an insert end and an outer end, an axial cavity in said body opening at one end onto the insert end of said body, said cavity being conical with it's base at the insert end and it's apex terminating short of and located closely adjacent to the outer end, at least one radial slot in the wall of the body surrounding the cavity, the slot extending from the insert end to the apex of the cavity and having a progressively reduced depth as it approaches the cavity apex.

7. The catamenial tampon recited in claim 1, wherein the body is comprised of a plurality of pads of shape-retaining moisture absorbent material drawn into a substantially cup-shaped configuration and compacted into the generally cylindrical shape.

8. The catamenial tampon recited in claim 7, wherein the slot opens onto the outside surface of the body in the area closely adjacent to the insert end.

9. The catamenial tampon recited in claim 8 wherein the body includes a layer of moisture impervious material sandwiched between the plurality of pads.

* * * * *